United States Patent

Heitsch et al.

Patent Number: 6,140,341
Date of Patent: Oct. 31, 2000

[54] AMINOALKYL AND ACYLAMINOALKYL ETHERS, PROCESS FOR THEIR PREPARATION, AND THEIR USE AS BRADYKININ RECEPTOR ANTAGONISTS

[75] Inventors: Holger Heitsch, Mainz-Kastel; Adalbert Wagner, Gersthofen; Klaus Wirth, Kriftel; Bernward Schölkens, Kelkheim; Gerhard Nölken, Sulzbach, all of Germany

[73] Assignee: Hoechst Aktiengesellschaft, Frankfurt am Main, Germany

[21] Appl. No.: 08/820,321

[22] Filed: Mar. 12, 1997

[30] Foreign Application Priority Data

Mar. 13, 1996 [DE] Germany ............... 196 09 827

[51] Int. Cl.⁷ ............... C07D 215/00; C07D 215/02; A61K 31/47

[52] U.S. Cl. ............... 514/311; 514/311; 514/314; 546/152; 546/176; 546/180; 546/182; 546/177; 546/171; 546/178

[58] Field of Search ............... 514/314; 546/152, 546/180, 171, 177, 182, 176, 178

[56] References Cited

U.S. PATENT DOCUMENTS

| | | | |
|---|---|---|---|
| 5,216,165 | 6/1993 | Mobilio et al. | 546/160 |
| 5,288,725 | 2/1994 | Witherup et al. | 514/292 |

FOREIGN PATENT DOCUMENTS

| | | |
|---|---|---|
| 0 622 361 | 11/1994 | European Pat. Off. |
| 9510513 | 4/1995 | WIPO ............... C07D 333/56 |
| 96/13485 | 5/1996 | WIPO . |
| 96/40639 | 12/1996 | WIPO . |
| 97/07115 | 2/1997 | WIPO . |

OTHER PUBLICATIONS

D. Hoyer et al., ACE inhibitors as a template for the design of bradykinin $B_2$ receptor antagonists, Chemical Abstracts, vol. 123(9): 111822x (1995).

*Primary Examiner*—Jose' G. Dees
*Assistant Examiner*—Sabiha N. Qazi
*Attorney, Agent, or Firm*—Finnegan, Henderson, Farabow, Garrett & Dunner, L.L.P.

[57] ABSTRACT

Aminoalkyl and acylaminoalkyl ethers which are distinguished by high affinity for the bradykinin $B_2$ receptor and improved solubility in water are described. These aminoalkyl and acylaminoalkyl ethers can be represented by the formula (I)

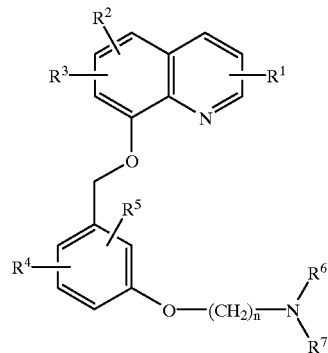

in which $R^1, R^2, R^3$ are alkyl, aryl, alkylaryl, halogen, hydrogen, cycloalkyl, CHO, CO—O-alkyl, COOH; $R^4$, $R^5$ are hydrogen, halogen, alkoxy, nitro, cyano, S-alkyl; n is a number from 1 to 8; $R^6$ is hydrogen, alkyl, alkylalkenyl, alkylaryl; $R^7$ is hydrogen and a substituted or unsubstituted acyl radical. A process for preparing the compounds of the formula (I) is likewise described.

38 Claims, No Drawings

AMINOALKYL AND ACYLAMINOALKYL ETHERS, PROCESS FOR THEIR PREPARATION, AND THEIR USE AS BRADYKININ RECEPTOR ANTAGONISTS

EP-A 622 361, U.S. Pat. No. 5,212,182, U.S. Pat. No. 5,216,165 and U.S. Pat. No. 5,438,064 disclose O- and N-substituted quinolines and their use as bradykinin receptor antagonists. Quinolines having substituents with an aminoalkyl ether and an acylaminoalkyl ether functionality in position 8 are not described.

The aminoalkyl and acylaminoalkyl ethers described in the present application are distinguished by high affinity for the bradykinin $B_2$ receptor and improved solubility in water and are represented by the formula (I)

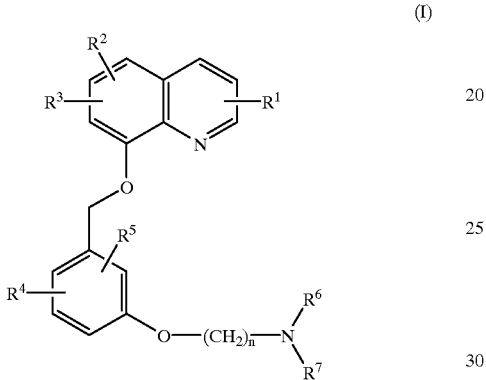

in which the symbols have the following meaning:

$R^1, R^2, R^3$ identical or different
  (1) $(C_1-C_5)$-alkyl,
  (2) $(C_6-C_{10})$-aryl,
  (3) $(C_1-C_3)$-alkyl-$(C_6-C_{10})$-aryl,
  (4) halogen,
  (5) hydrogen,
  (6) $(C_3-C_8)$-cycloalkyl,
  (7) CHO,
  (8) CO—O—$(C_1-C_3)$-alkyl
  (9) COOH;

$R^4, R^5$ identical or different
  (1) hydrogen,
  (2) halogen,
  (3) $(C_1-C_3)$-alkoxy,
  (4) nitro,
  (5) cyano,
  (6) S-$(C_1-C_3)$-alkyl;

n a number from 1 to 8;

$R^6$
  (1) hydrogen,
  (2) $(C_1-C_3)$-alkyl,
  (3) $(C_3-C_5)$-alkylalkenyl,
  (4) $(C_1-C_3)$-alkyl-$(C_6-C_{10})$-aryl;

$R^7$ hydrogen and the following substituted or unsubstituted acyl radicals:
  $(C_1-C_6)$-alkanoyl (for example formyl, acetyl, propionyl etc.), $(C_1-C_3)$-alkoxy-$(C_2-C_6)$-alkanoyl (for example methoxyacetyl, ethoxyacetyl etc.), $(C_1-C_6)$-alkylcarbamoyl-$(C_2-C_6)$-alkanoyl (for example methylcarbamoylacetyl etc.), $(C_6-C_{12})$-aryl-$(C_2-C_6)$-alkanoyl (for example phenylacetyl, tolylacetyl etc.), $(C_3-C_7)$-alkenoyl (for example acryloyl, crotonoyl etc.), $(C_3-C_8)$-cycloalkylcarbonyl (for example cyclopropylcarbonyl, cyclohexylcarbonyl etc.), $(C_5-C_7)$-cycloalkenylcarbonyl (for example cyclohexenylcarbonyl etc.), $(C_1-C_3)$-alkoxycarbonyl (for example methoxycarbonyl, ethoxycarbonyl etc.), $(C_6-C_{12})$-aryloxycarbonyl (for example phenoxycarbonyl etc.), $(C_6-C_{12})$-aroyl (for example benzoyl, naphthoyl etc.), $(C_1-C_3)$-alkoxy-$(C_6-C_{12})$-aroyl (for example methoxybenzoyl etc.), halogen-$(C_6-C_{12})$-aroyl (for example chlorobenzoyl etc.), $(C_6-C_{12})$-aryl-$(C_3-C_6)$-alkenoyl (for example cinnamoyl, allocinnamoyl, α-methylcinnamoyl, 4-methylcinnamoyl etc.), $(C_1-C_3)$-alkoxy-$(C_6-C_{12})$-aryl-$(C_3-C_6)$-alkenoyl (for example methoxycinnamoyl, ethoxycinnamoyl, dimethoxycinnamoyl etc.), $(C_1-C_3)$-alkylenedioxy-$(C_6-C_{12})$-aryl-$(C_3-C_6)$-alkenoyl (for example methylenedioxycinnamoyl etc.), nitro-$(C_6-C_{12})$-aryl-$(C_3-C_6)$-alkenoyl (for example nitrocinnamoyl etc.), cyano-$(C_6-C_{12})$-aryl-$(C_3-C_6)$-alkenoyl (for example cyanocinnamoyl etc.), halo-$(C_6-C_{12})$-aryl-$(C_3-C_6)$-alkenoyl (for example chlorocinnamoyl, dichlorocinnamoyl etc.), halo-$(C_1-C_3)$-alkyl-$(C_6-C_{12})$-aryl-$(C_3-C_6)$-alkenoyl (for example trifluoromethylcinriamoyl), hetero-$(C_3-C_8)$-cycloalkyl-$(C_6-C_{12})$-aryl-$(C_3-C_6)$-alkenoyl (for example morpholinocinnamoyl etc.), amino-$(C_6-C_{12})$-aryl-$(C_3-C_6)$-alkenoyl (for example aminocinnamoyl), $(C_1-C_4)$-alkylamino-$(C_6-C_{12})$-alyl-$(C_3-C_6)$-alkenoyl, (for example methylaminocinnamoyl, dimethylaminocinnamoyl etc.), $(C_2-C_5)$-acylamino-$(C_6-C_{12})$-arylcinnamoyl (for example acetylaminocinnamoyl, cyclopropylcarbonylaminocinnamoyl etc.), $(C_1-C_3)$-alkoxycarbonylamino-$(C_6-C_{12})$-arylcinnamoyl (for example methoxycarbonylaminocinnamoyl etc.), $(C_1-C_4)$-alkylaminocarbonylaminocinnamoyl (for example ethylaminocarbonylaminocinnamoyl), hetero-$(C_6-C_{12})$-aryl-$(C_2-C_6)$-alkanoylamino-$(C_6-C_{12})$-aryl-$(C_3-C_6)$-alkenoyl (for example pyridylacetylaminocinnamoyl etc.), $(C_6-C_{12})$-aroylamino-$(C_6-C_{12})$-aryl-$(C_3-C_6)$-alkenoyl (for example benzoylaminocinnamoyl etc.), hetero-$(C_6-C_{12})$-arylcarbonylamino-$(C_6-C_{12})$-aryl-$(C_3-C_6)$-alkenoyl (for example pyridylcarbonylaminocinnamoyl etc.), $(C_1-C_5)$-alkylsulfonylamino-$(C_6-C_{12})$-aryl-$(C_3-C_6)$-alkenoyl (for example ethylsulfonylaminocinnamoyl etc.), $(C_1-C_5)$-alkylureido-$(C_6-C_{12})$-aryl-$(C_3-C_6)$-alkenoyl (for example ethylureidocinnamoyl etc.), $(C_2-C_6)$-alkanoyl-$(C_6-C_{12})$-aryl-$(C_3-C_6)$-alkenoyl (for example acetylcinnamoyl), $(C_1-C_5)$-alkoxycarbonyl-$(C_6-C_{12})$-aryl-$(C_3-C_6)$-alkenoyl (for example methoxycarbonylcinnamoyl etc.), $(C_1-C_5)$-alkylcarbamoyl-$(C_6-C_{12})$-aryl-$(C_3-C_6)$-alkenoyl (for example ethylcarbamoylcinnamoyl etc.), $(C_6-C_{12})$-arylcarbamoyl-$(C_6-C_{12})$-aryl-$(C_3-C_6)$-alkenoxyl (for example phenylcarbamoylcinnamoyl etc.), $(C_6-C_{12})$-aryl-$(C_1-C_5)$-alkoxycarbonyl (for example benzyloxycarbonyl etc.), $(C_1-C_5)$-alkylcarbamoyl (for example ethylcarbamoyl etc.), $(C_6-C_{12})$-arylcarbamoyl (for example phenylcarbamoyl), $(C_6-C_{12})$-aroylcarbamoyl (for example benzoylcarbamoyl etc.), $(C_1-C_6)$-alkylsulfonyl (for example mesyl, ethylsulfonyl etc.), $(C_6-C_{12})$-arylsulfonyl (for example phenylsulfonyl etc.), $(C_6-C_{12})$-aryl-$(C_1-C_6)$-alkylsulfonyl (for example benzylsulfonyl etc.) and or $R^6$ and $R^7$ together represent a phthaloyl group which forms a ring with the nitrogen atom, and their physiologically tolerated salts.

Alkyl, alkenyl and alkynyl can be straight-chain or branched. A corresponding statement applies to radicals derived therefrom, such as, for example, alkoxy.

($C_6$–$C_{12}$)-aryl is preferably phenyl, naphthyl or biphenyl. A corresponding statement applies to radicals derived therefrom, such as aryloxy, aralkyl or aroyl.

Heteroaryl means radicals which have up to 9 carbon atoms and form a monocyclic or bicyclic aromatic ring in which one or more CH groups are replaced by N, O and/or S. Examples of these are thienyl, furanyl, imidazolyl, oxazolyl, isoxazolyl, pyridyl, pyrimidyl, indolyl, quinolyl, imidazopyridyl.

Halogen is fluorine, chlorine, bromine and iodine, preferably chlorine.

Physiologically tolerated salts of compounds of the formula (I) means both their organic and their inorganic salts as described in Remington's Pharmaceutical Sciences (A. R. Gennaro (Editor), Mack Publishing Co., Easton, Pa., 17th Edition, page 1418 (1985)). Because of the physical and chemical stability and the solubility, preferred for acidic groups are sodium, potassium, calcium and ammonium salts inter alia; preferred for basic groups are other salts with hydrochloric acid, sulfuric acid, phosphoric acid, or of carboxylic acids or sulfonic acids, such as, for example, acetic acid, citric acid, benzoic acid, maleic acid, fumaric acid, tartaric acid and p-toluenesulfonic acid.

Preferred compounds of the formula (I) are those in which the symbols have the following meaning:

$R^1$, $R^2$, $R^3$ identical or different
(1) hydrogen,
(2) ($C_1$–$C_3$)-alkyl;
$R^4$, $R^5$ halogen;
$R^6$
(1) hydrogen,
(2) methyl, ethyl
(3) benzyl;
and the other radicals and variables are as defined above.

Particularly preferred compounds of the formula (I) are those in which the symbols have the following meaning:

$R^7$
(1) hydrogen,
(2) an acyl radical such as ($C_2$–$C_6$)-alkanoyl, ($C_6$–$C_{12}$)-aryl-($C_2$–$C_6$)-alkanoyl, ($C_6$–$C_{12}$)-aryl-($C_2$–$C_6$)-cycloalkanoyl, ($C_1$–$C_6$)-alkylaminocarbonyl, ($C_3$–$C_7$)-alkenylaminocarbonyl, ($C_1$–$C_3$)-alkoxycarbonyl, ($C_6$–$C_{12}$)-aryl-($C_1$–$C_6$)-alkylaminocarbonyl, ($C_6$–$C_{12}$)-aryl-($C_3$–$C_6$)-alkenoyl, ($C_1$–$C_3$)-alkoxy-($C_6$–$C_{12}$)-aryl-($C_3$–$C_6$)-alkenoyl, halo-($C_6$–$C_{12}$)-aryl-($C_3$–$C_6$)-alkenoyl, halo-($C_1$–$C_3$)-alkyl-($C_3$–$C_6$)-alkenoyl, amino-($C_6$–$C_{12}$)-aryl-($C_3$–$C_6$)-alkenoyl, ($C_1$–$C_6$)-alkylamino-($C_3$–$C_6$)-alkenoyl, and hetero-($C_6$–$C_{12}$)-aryl-($C_3$–$C_6$)-alkenoyl and phthaloyl (for $R^6$=$R^7$);
and the other radicals and variables are as defined above.

Very particularly preferred compounds of the formula (I) are those in which the symbols have the following meaning:

$R^1$, $R^2$, $R^3$ identical or different
(1) hydrogen,
(2) methyl, ethyl, propyl;
$R^4$, $R^5$ chlorine;
n 1 to 4;
$R^6$ hydrogen;
$R^7$
(1) hydrogen,
(2) ($C_2$–$C_5$)-alkanoyl,
(3) ($C_3$–$C_5$)-alkenoyl,
(4) ($C_1$–$C_5$)-alkylaminocarbonyl,
(5) ($C_6$–$C_{10}$)-aryl-($C_1$–$C_3$)-alkylaminocarbonyl,
(6) ($C_1$–$C_5$)-alkyloxycarbonyl,
(7) ($C_6$–$C_{10}$)-aryl-($C_1$–$C_3$)-alkyloxycarbonyl,
(8) ($C_6$–$C_{10}$)-aryl-($C_3$–$C_7$)-cycloalkylcarbonyl,
(9) a trans-cinnamic acid residue whose phenyl ring is substituted by up to 2 identical or different radicals from the series
a) hydrogen,
b) ($C_1$–$C_3$)-alkyl,
c) amino,
d) ($C_1$–$C_3$)-mono- and -dialkylamino,
e) halogen,
f) ($C_1$–$C_3$)-haloalkyl,
g) ($C_2$–$C_5$)-acylamino and
h) ($C_1$–$C_3$)-alkoxy.

The invention furthermore relates to a process for preparing compounds of the formula (I), which comprises
a) reacting a compound of the formula (II)

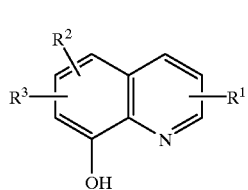

(II)

in which $R^1$, $R^2$ and $R^3$ are as defined above, with a compound of the formula(III)

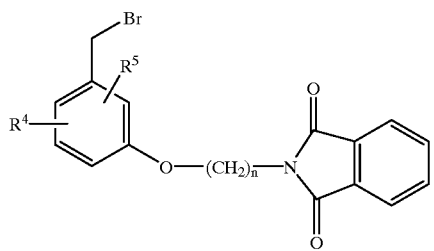

(III)

in which $R^4$, $R^5$ and n are as defined above, in the presence of metal hydrides such as lithium, potassium or sodium hydride, or alkali metal carbonates such as sodium, potassium or cesium carbonate, in an inert solvent such as DMF or DMSO, at temperatures from 0° C. to 60° C. to give a compound of the formula (IV)

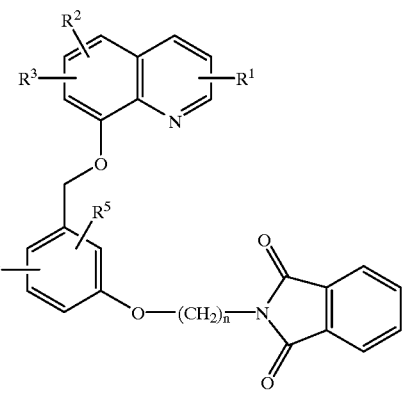

(IV)

where the symbols and variables are as defined above;

b) converting a compound of the formula (IV) by hydrazinolysis in ethanol under reflux into a compound of the formula (Ia),

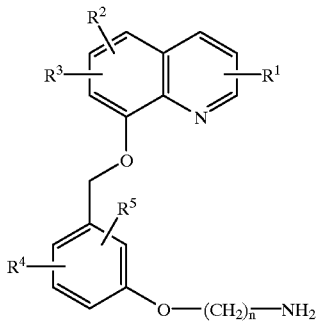

(Ia)

in which $R^1$, $R^2$, $R^3$, $R^4$, $R^5$ and n are as defined above;

c) where appropriate acylating and/or alkylating the compounds of the formula (Ia) by known methods, and d) where appropriate converting the resulting compounds of the formula (I) into their physiologically tolerated salts by known methods.

The compounds of the formula (Ia) are acylated by reaction with the appropriately substituted carboxylic acids and sulfonic acids or their activated derivatives and isocyanates.

Suitable activated acid derivatives in this case as acid chlorides, anhydrides and active esters, for example, carbonyl chlorides and bromides, mixed anhydrides, symmetrical anhydrides, p-nitrophenyl esters and hydroxysuccinimide esters. The choice of one of these activated derivatives depends on the acyl group to be introduced.

In the case of the free acids, the acylation takes place in the presence of the condensation reagents used in peptide chemistry, see, for example, Houben-Weyl, Methoden der Organischen Chemie [Methods of Organic Chemistry], Volume 15/2, Georg Thieme Verlag, Stuttgart 1974, but especially carbodiimides such as, for example, N,N'-dicyclohexylcarbodiimide, N,N'-diisopropylcarbodiimide and N-ethyl-N'-(3-dimethylaminopropyl)carbodiimide or uronium salts such as O-[cyano-(ethoxycarbonyl) methyleneamino]-1,1,3,3-tetramethyluronium tetrafluoroborate (TOTU) and O-benzotriazol-1-yl-N,N,N',N'-tetramethyluronium hexafluorophosphate (HBTU).

The acylation or activation of the acid derivatives takes place in conventional organic solvents such as $CH_2Cl_2$, dioxane, THF or DMF. The acylation is carried out in the presence of an inorganic or organic base at temperatures from 0° C. to reflux.

Processes for preparing compounds of the formula (II) are disclosed, inter alia, in H. Fiedler, J. Prakt. Chemie, Vol. 13, 1961, 86 et seq.

The compounds of the formula (III) are prepared by halogenating the corresponding methyl compounds of the formula (V)

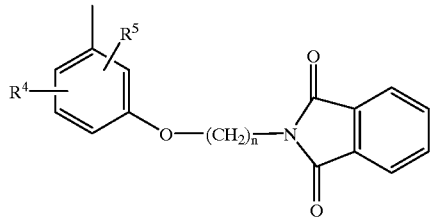

(V)

in which $R^4$, $R^5$ and n are as defined above, preferably with N-bromosuccinimide or 1,3-dibromo-5,5-dimethylhydantoin in chlorobenzene under reflux.

Compounds of the formula (V) are prepared by alkylating the phenols of the formula (VI)

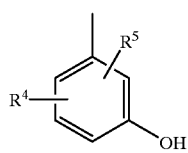

(VI)

in which $R^4$ and $R^5$ are as defined above, with commercially obtainable N-(bromoalkyl)phthalimides in the presence of alkali metal carbonates such as sodium, potassium or cesium carbonate in DMSO as solvent at room temperature with reaction times of from 10 min to 1 h.

The compounds of the formula (I) according to the invention have, singly or in combination, a bradykinin-antagonistic effect which can be tested in various models (see Handbook of Exp. Pharmacol. Vol. 25, Springer Verlag, 1970, pages 53–55), for example on isolated rat uterus, on guinea pig ileum, on isolated guinea pig pulmonary artery or on rabbit jugular vein.

The effects of the compounds of the formula (I) on the bradykinin-induced bronchoconstriction and on carrageenin-induced paw oedema can be determined in analogy to the procedure described in Br. J. Pharmacol., 102, 774–777 (1991).

Determination of the affinity of the compounds of the formula (I) for the bradykinin $B_2$ receptor took place on preparations of membranes from the guinea pig ileum (R. B. Innis et al., Proc. Natl. Acad. Sci. USA; 17 (1981) 2630) by the following method:

1. Ligand: $^3$H-BRADYKININ (from NEN Du Pont)
2. Buffer Mixtures:
   a) TES Buffer:
   25 mM TES (SIGMA, Order No.: T-4152)
   1 mM 1,10-phenanthroline (SIGMA; Order No.: P-9375)
   b) Incubation Buffer:
   25 mM TES (SIGMA; Order No.: T-4152)
   1 mM 1,10-phenanthroline (SIGMA; Order No.: P-9375)
   0.1% albumin, bovine (SIGMA; Order No.: A-7906)
   140 µg/ml bacitracin (SIGMA; Order No.: B-0125)
   1 mM dithiothreitol (SIGMA; Order No.: D-0632)
   1 µM captopril-1-[(2S)-3-mercapto-2-methylpropionyl]-L-proline
   Both buffers are adjusted to pH 6.8 with 5 molar NaOH.

3. Membrane Preparation:

Guinea pig ilea are carefully squeezed out to remove most of the intestinal contents and are cleaned in 0.9% strength NaCl solution.

The pieces of ilea about 2 cm long are transferred into ice-cold TES buffer (about 1 g/10 ml) and homogenized with an Ultraturrax in an ice bath for about 30 sec. The homogenate is then filtered through 3 layers of gauze and the filtrate is centrifuged at 50,000 g for 10 minutes.

The supernatant is discarded, and the pellet is rehomogenized in the same volume of TES buffer and again centrifuged at 50,000 g for 10 minutes. The pellet is rehomogenized in incubation buffer (about 1 g/5 ml) and frozen in 2 ml portions in cryotubes at −70° C.

The protein concentration in the finished membrane suspension is determined by the LOWRY method and should be about 15 μg/100 μl.

4. Binding Assay:

All the incubations are carried out in a volume of 200 μl in microtiter plates (96×300 μl) at room temperature for 60 minutes. All mixtures in incubation bufler. 50 μl of the radioligands, 50 μl of the product to be tested and 100 μl of the membrane suspension are successively pipetted into these in the wells of the microtiter plate.

a) Saturation experiments (hot saturation):

Preparation of the $^3$H-bradykinin solution: The concentrations employed for the saturation experiments are 0.05, 0.1, 0.2, 0.4, 0.6, 0.8, 1.0, 1.5, 2.0, 2.5 and 3.0 nMol/l, equivalent to 0.05 to 3.0 pMol/ml. After preparation of the appropriate dilutions, 50 μl of each are introduced per sample.

Nonspecific binding: The nonspecific binding must be determined for each concentration of the radioactive ligand. This can be achieved by adding a high concentration (1–100 μMol) of the unlabeled ligand, other antagonists or agonists of the bradykinin receptor. HOE 140 (10 μMol/l) is used in this assay. For this purpose, 1.862 mg are dissolved in 1 ml of dimethyl sulfoxide (DMSO) and diluted 1:25 with incubation buffer, and 50 μl of this solution are added to the samples in the microtiter plate. The reaction is started by adding 100 μl of the membrane suspension.

b) Competition experiments ($IC_{50}$):

In this case, a fixed magnitude of the radioactive ligand (0.25 to 0.3 nMol/l $^3$H-bradykinin) and various concentrations of the unlabeled agonists or antagonists are employed.

50 μl of the products to be tested or of the standard are added in concentrations from $10^{-5}$ bis $10^{-10}$ Mol/l to, in each case, 50 μl of the $^3$H-bradykinin solution, and the reaction is started by adding 100 μl of membrane suspension. Triplicate determinations are also carried out in this assay, and three samples are incubated with 10 μMol/l HOE 140 to determine the nonspecific binding.

The products to be tested for competition are always dissolved at a concentration of 1 mMol/l in dimethyl sulfoxide (DMSO) and subsequently further diluted with DMSO. This solution is then diluted 1:25 with incubation buffer.

After the incubation, the samples are filtered in a Skatron cell harvester through a Whatman GF/B filter paper strip which has previously been moistened with 0.1% PEI (polyethyleneimine) and washed with 10 ml of ice-cold TES buffer per sample. The still moist filters are punched out into mini scintillation tubes and 3 ml of scintillator are added.

After an extraction time of about 12 hours, the samples are briefly shaken and measured in the beta counter.

c) Screening:

In primary screening, generally only 1-2 concentrations of the test product ($10^{-5}$ and $10^{-6}$ mol/l) are employed. If 50% or more displacement of the radiolic and is detectable with the highest concentration, a complete analysis (competition experiment) is carried out with at least 8 concentrations.

4. Evaluation:

The evaluation takes place using the LIGAND program package (McPherson, Minson & Rodbard, marketed by Elsevier-BIOSOFT), which carries out the calculations needed to determine $IC_{50}$ and $K_i$ values. This program additionally performs graphical representations of the saturation and displacement plots and of the SCATCHARD plot, HILL plot or HOFSTEE plot.

5. Assay results

The following $K_i$ value are determined by the abovementioned method for the compounds of Examples 2, 5 and 6 as representative compounds of the aminoalkyl and acylaminoalkyl ethers of the formula (I) described:

| Example | $K_i$ [nM] |
| --- | --- |
| 2 | 20 |
| 5 | 61 |
| 6 | 32 |

Furthermore, to determine the bradykinin-antagonistic effect of the compounds of the formula (I) it is possible to measure their effect on the bradykinin-induced contraction of the guinea pig ileum by the following protocol:

Guinea pigs weighing about 300 g (Morioth strain,__) are sacrificed by a blow to the back of the neck and are exsanguinated. A length of about 20 cm of ileum is dissected out and rinsed with Tyrode solution (Record syringe), thus removing intestinal contents. It is then divided into segments 1.5 cm long. These are fixed in organ baths with a capacity of 10 ml which are filled with Tyrode solution, and are connected to strain gauges (isometric contraction measurement). The initial load is 1 g. The Tyrode solution is heated in a water bath to 37° C., and compressed air is bubbled through.

After an interval of 30 min, the experiment is started. After recording the biological zero line, bradykinin is added to each organ bath in a final concentration of $4 \times 10^8$ mol/l, and the concentration is recorded. Then, after rinsing with Tyrode solution for 3 min and a resting period of 20 min, bradykinin is again added. The maximum contraction is reached (control). Rinsing and resting period repeated. The bradykinin antagonist is then added (action time 10 min.). Bradykinin is then added again and the contraction which now takes place is compared with that of the control. The experiment is recorded on a pen recorder.

Tyrode solution (mM):

| | |
| --- | --- |
| NaCl | 137 |
| Glucose | 5.05 |
| KCl | 2.68 |

-continued

| | |
|---|---|
| NaHCO$_3$ | 11.9 |
| NaH$_2$PO$_4$ | 0.47 |
| MgCl$_2$ × 2H$_2$O | 0.49 |
| CaCl$_2$ × 2H$_2$O | 0.68 |

Amplifier: TF6 V3 From Fleck, Mainz
Pen recorder: Goerz Metrawatt SE 460, BBC
Bradykinin: from Bachem Thus, for example, the compound of Example 1 has the following IC$_{50}$ determined by the above method: IC$_{50}$=1.8× 10$^{-6}$ M.

For an oral administration form or for administration onto the mucous membranes, the active compounds are mixed with the additives customary for this purpose, such as excipients, stabilizers or inert diluents and converted by customary methods into suitable dosage forms such as tablets, coated tablets, hard gelatin capsules, aqueous, alcoholic or oily suspensions or aqueous, alcoholic or oily solutions. Examples of inert vehicles which can be used are gum arabic, magnesia, magnesium carbonate, potassium phosphate, lactose, glucose, magnesium stearyl- fumarate or starch, especially corn starch. Preparation can take place either as dry or wet granules. Examples of suitable oily excipients or solvents are vegetable or animal oils, such as sunflower oil and fish liver oil.

A product for topical administration can be in the form of an aqueous or oily solution, lotion, emulsion or gel, ointment or fatty ointment or, if possible, in spray form, it being possible where appropriate to improve the adhesion by adding a polymer.

For an intranasal administration form, the compounds are mixed with the additives customary for this purpose, such as stabilizers or inert diluents, and converted by customary methods into suitable dosage forms such as aqueous, alcoholic or oily suspensions or aqueous, alcoholic or oily solutions. It is possible to add to aqueous intranasal preparations chelating agents, ethylenediamine-N,N,N',N'-tetraacetic acid, citric acid, tartaric acid or their salts. Administration of the nasal solutions can take place using a metering atomizer or as nose drops with viscosity-increasing content, or nasal gels or nasal creams.

The compounds of the formula (I) described, and their pharmacologically suitable salts, are potent bradykinin antagonists. Their therapeutic use is therefore for the treatment and/or prevention of all pathological conditions mediated, induced or assisted by bradykinin and peptides analogous to bradykinin. These include, inter alia, allergies, inflammations, autoimmune diseases, shock, pain and, more specifically, asthma, cough, bronchitis, rhinitis, chronic obstructive pulmonary disorders, pneumonitis, septic shock, endotoxic shock, anaphylactic shock, disseminated intravascular coagulation, arthritis, rheumatism, osteoarthritis, lumbago, inflammation-induced bone resorption, conjunctivitis, iritis, headache, migraine, toothache, backache, cancer pain, postoperative pain, traumata (wounds, burns, etc.), rash, erythemas, edemas, eczemas, dermatitis, zoster, herpes, pruritus, psoriasis, lichen, inflammatory bowel disorders, hepatitis, pancreatitis, gastritis, esophagitis, food allergies, ulcers, irritable colon, angina, cerebral edema, low blood pressure, thrombosis, cranioce-rebral and spinal trauma, premature birth, atherosclerosis, ascites associated with malignant cancer, tumor metastases, cerebral edema associated with tumors, heat damage to the brain and viral diseases.

Since it is furthermore known that bradykinin is linked to the release of mediators such as prostaglandins, leukotrienes, tachykinins, histamine, thromboxanes, the compounds of the formula (I) thus also have the potential to treat ancd/or prevent diseases caused by these mediators.

The invention therefore also relates to the use of compounds of the formula (I) as medicines and to pharmaceutical products which contain these compounds.

Pharmaceutical products and medicines contain an effective amount of the active substance of the formula (I)—singly or in combination—together with an inorganic or organic excipient which can be used in pharmacy.

Administration can take place enterally, parenterally, such as, for example, subcutaneously, i.m. or i.v., sublingually, epicutaneously, nasally, rectally, intravaginally, intrabuccally or by inhalation. The dosage of active substance depends on the warm-blooded species, the bodyweight, age and mode of administration.

The pharmaceutical products of the present invention are produced in dissolving, mixing, granulating or coating processes known per se.

For administration by inhalation it is possible to employ atomizers or compressed gas packs using inert carrier gases.

For intravenous, subcutaneous, epicutaneous or intradermal administration, the active compounds or their physiologically tolerated salts are converted, if required with pharmaceutically customary ancillary substances, for example for isotonisization or pH adjustment, in solubilizers, emulsifiers or other ancillary substances, into a solution, suspension or emulsion.

If the half-lives of the described medicinal substances in body fluids are inadequate, it is worthwhile to use injectable depot preparations.

Examples of medicinal forms which can be used as oily crystal suspensions, microcapsules, rods or implants, it being possible for the latter to be composed of tissue-compatible polymers, especially biodegradable polymers, for example based on polylactic acid/polyglycolic acid copolymers or human albumin.

A suitable dose range for forms for administration topically and by inhalation is 0.01–5 mg/l of solution, and 0.01–10 mg/kg are suitable for forms for systemic administration.

It is generally possible to administer amounts between 0.1 mg/kg and 1000 mg/kg of bodyweight.

List of abbreviations:

| | |
|---|---|
| CH$_2$Cl$_2$ | dichloromethane |
| DCI | desorption chemical ionisation |
| DIP | diisopropyl ether |
| DMF | N,N-dimethylformamide |
| EA | ethyl acetate |
| FAB | fast atom bombardment |
| h | hour(s) |
| MeOH | methanol |
| Min | minute(s) |
| RT | room temperature |
| TOTU | O-[cyano(ethoxycarbonyl)methyleneamino]-1,1,3,3-tetramethyluronium tetrafluoroborate |
| Decomp. | decomposition |

The invention is illustrated by the following examples.

EXAMPLE 1

8-[3-(2-aminoethoxy)-2,6-dichlorobenzyloxy]-2-methylquinoline a) 2,6-dichloro-3-(2-phthaloylethoxy)toluene 5.0 g (28.2 mmol) of 2,4-dichloro-3-methylphenol and 9.2 g (28.2 mmol) of $Cs_2CO_3$ in 100 ml of DMSO were stirred at RT for 10 min. 7.5 g (28.2 mmol) of N-(2-bromoethyl)phthalimide were added and the resulting reaction mixture was stirred at RT for 16 h.

$H_2O$ was added and the reaction solution was extracted several times with EA. The organic phases were combined, washed with 1 N NaOH, 1 N HCl, $H_2O$ and saturated NaCl solution and dried over $Na_2SO_4$. Filtration, stripping off the solvent and chromatography on silica gel with EA/n-heptane 1:4 afforded 2.9 g of the title compound.

Melting point: 148° C.; $R_f$ ($SiO_2$, EA/n-heptane 1:4)=0.15 MS (DCl): 350 (M+H)

b) 2,6-dichloro-3-(2-phthaloylethoxy)benzyl bromide

A solution of 1.9 g (5.4 mmol) of the compound from Example 1a), 1.0 g (5.4 mmol) of N-bromosuccinimide and 50 mg of benzoyl peroxide in 20 ml of chlorobenzene was heated under reflux for 2 h. It was evaporated to dryness and the residue was taken up in $CH_2Cl_2$. The resulting $CH_2Cl_2$ solution was washed with saturated $NaHCO_3$ solution and $H_2O$ and dried over $Na_2SO_4$. It was evaporated to dryness and the residue was recrystallized from EA. The crystals were filtered off with suction and dried under high vacuum to afford 1.9 g of the title compound.

Melting point: 171° C.; $R_f$ ($SiO_2$, EA/n-heptane 1:2)=0.19 MS (DCl): 428/430 (M+H)

c) 8-[2,6-dichloro-3-(2-phthaloylethoxy)benzyloxy]-2-methylquinoline 700.0 mg (4.3 mmol) of 8-hydroxy-2-methylquinoline were added in portions at 0° C. to a suspension of 207.0 mg (4.3 mmol) of a 50% dispersion of NaH in mineral oil in 30 ml of abs. DMF. The mixture was stirred at 0° C. for 30 min. and 1.85 g (4.3 mmol) of the compound from Example 1b) were added, likewise in portions. After stirring at 0° C. for 1 h, the reaction solution was evaporated to dryness, and the residue was suspended in a little $H_2O$ and extracted several times with $CH_2Cl_2$. The combined organic extracts were dried over $Na_2SO_4$, filtered and concentrated. The resulting residue was recrystallized from EA. The white crystals were filtered off with suction and dried to afford 2.0 g of the title compound.

Melting point: 176° C.; $R_f$ ($SiO_2$, EA/n-heptane 1:2)=0.13 MS (DCl)=507 (M+H)

d) 8-[3-(2-aminoethoxy)-2,6-dichlorobenzyloxy]-2-methylquinoline A solution of 1.8 g (3.5 mmol) of the compound from Example 1c) and 350 µl (7.2 mmol) of hydrazine hydrate in 30 ml of ethanol was heated under reflux for 1.5 h. It was evaporated to dryness, the resulting residue was suspended in water, and the suspension was, after addition of 2 N NaOH (pH~12) extracted several times with $CH_2Cl_2$. Drying over $Na_2SO_4$, stripping off the solvent and purification by chromatography on silica gel with EA/MeOH/$NH_4OH$=8:2:0.1 afforded 1.3 g of the title compound.

Melting point: 123–125° C.; $R_f$ (EA/MeOH/$NH_4OH$ 8:2:0.1)=0.16 MS (DCl)=377 (M+H)

EXAMPLE 2

8-[3-(2-N-(trans-4-aminocinnamoyl)aminoethoxy)-2,6-dichlorobenzyloxy]-2-methylquinoline a) 8-[3-(2-(trans-4-(N-tert-butyloxycarbonyl)aminocinnamoyl)aminoethoxy)benzyloxy]-2-methylquinoline A solution of 120.0 mg (0.32 mmol) of the compound from Example 1a), 83.5 mg (0.32 mmol) of trans-4-(N-tert-butyloxycarbonylamino)cinnamic acid, 56.0 µl of N-ethyldiisopropylamine and 106.3 mg (0.32 mmol) of TOTU in 5 ml of abs. DMF was stirred at RT for 3 h. It was evaporated to dryness under high vacuum, the residue was taken up in $CH_2Cl_2$/water and the organic phase was separated off. It was washed with 10% strength $KHSO_4$ and 10% $NaHCO_3$ solutions and dried over $Na_2SO_4$. Filtration, stripping off the solvent and purification by chromatography on $SiO_2$ with EA/heptane 2:1 afforded 130 mg of the title compound.

Melting point: 116–118° C.; $R_f$ (EA/n-heptane 4:1)=0.27 MS (FAB): 622 (M+H)

b) 8-[3-(2-N-(4-trans-aminocinnamoyl)aminoethoxy)-2,6-dichlorobenzyloxy]-2-methylquinoline A solution of 65.0 mg (0.10 mmol) of the compound from Example 2a) and 260 µl of trifluoroacetic acid in 5 ml of $CH_2Cl_2$ was stirred at RT for 5 h. It was evaporated to dryness, and the residue was taken up in toluene and again evaporated to dryness several times. The remaining residue was taken up in a little MeOH and the title compound was crystallized by adding diisopropyl ether. 60 mg of the title compound were isolated as bistrifluoroacetate.

Melting point: 158° C. (decomp.); $R_f$ (EA/n-heptane 10:1)=0.18 MS (FAB): 522 (M+H)

EXAMPLE 3

8-[2,6-dichloro-3-(2-(N-ethylaminocarbonylamino)ethoxy)benzyloxy]-2-methylquinoline 80.0 mg (0.21 mmol) of the compound from Example 1d) and 33.0 µl (0.42 mmol) of ethylisocyanate in 2 ml of $CH_2Cl_2$ were stirred at RT for 1.5 h. The residue after evaporation to dryness was triturated with a little EA. The title compound resulted as a white precipitate, which was filtered off with suction and washed with a little cold EA. Drying under high vacuum afforded 70 mg of the required compound.

Melting point: 153–154° C.; $R_f$ (EA/n-heptane 1:2)=0.49 MS (DCl): 448 (M+H)

EXAMPLE 4

8-[2,6-dichloro-3-(2-(3-phenylpropionylamino)ethoxy)benzyloxy]-2-methylquinoline 90.0 mg (0.24 mmol) of the compound from Example 1d), 35.8 mg (0.24 mmol) of 3-phenylpropionic acid, 42.0 µl (0.24 mmol) of N-ethyldiisopropylamine and 80.0 mg (0.24 mmol) of TOTU in 5 ml of abs. DMF were reacted by the process indicated in Example 2a). Chromatography on $SiO_2$ with EA/n-heptane 2:1 as mobile phase resulted in 60.0 mg of the title compound.

Melting point: 112–114° C.; $R_f$ ($SiO_2$, EA/n-heptane 2:1)=0.12 MS (DCl): 509 (M+H)

EXAMPLE 5

8-[2,6-dichloro-3-(trans-2-N-cinnamoylaminoethoxy)benzyloxy]-2-methylquinoline 100.0 mg (0.26 mmol) of the compound from Example 1d), 39.3 mg (0.26 mmol) of trans-cinnamic acid, 46.6 µl (0.26 mmol) of N-ethyl-diisopropylamine and 88.8 mg (0.26 mmol) of TOTU were reacted in 5 ml of abs. DMF by the process indicated in Example 2a). Chromatography on $SiO_2$ (EA/n-heptane 2:1) resulted in 90 mg of the title compound.

Melting point: 170–171° C.; $R_f$ (EA/n-heptane 2:1)=0.13 MS (DCI): 507 (M+H)

EXAMPLE 6

8-[2,6-dichloro-3-(2-N-(trans-4-methoxycinnamoyl)aminoethoxy)benzyloxy]-2-methylquinoline 100.0 mg (0.26 mmol) of the compound from Example 1d), 47.2 mg (0.26 mmol) of trans-p-methoxycinnamic acid, 46.6 µl (0.26 mmol) of N-ethyldiisopropylamine and 88.8 mg (0.26 mmol) of TOTU were reacted in 5 ml of abs. DMF in analogy to the process indicated in Example 2a). 69 mg of the title compound resulted.

Melting point: 182° C.; $R_f$ (EA/n-heptane 2:1)=0.12 MS (DCI): 537 (M+H)

EXAMPLE 7

8-[2,6-dichloro-3-(2-(N-(trans-2-phenylcyclopropane-1-carbonylamino)-ethoxy)benzyloxy]-2-methylquinoline 100.0 mg (0.26 mmol) of the compound from Example 1d), 43.0 mg (0.26 mmol) of trans-2-phenylcyclopropane-1-carboxylic acid, 46 µl (0.26 mmol) of N-ethyldiisopropylamine and 88.8 mg (0.26 mmol) of TOTU were reacted in accordance with the process indicated in Example 2a). 65 mg of the title compound were obtained.

Melting point: 108° C. (decomp.); $R_f$ ($SiO_2$, EA/n-heptane 2:1)=0.15 MS (DCI): 521 (M+H)

EXAMPLE 8

8-[2,6-dichloro-3-(2-N-(trans-3-methoxycinnamoyl)aminoethoxy)-benzyloxy]-2-methyquinoline 100.0 mg (0.26 mmol) of the compound from Example 1d) were reacted with 47.2 mg (0.26 mmol) of trans-m-methoxycinnamic acid in accordance with the process indicated in Example 2a). 55.0 mg of the title compound resulted.

Melting point: 158–159° C.; $R_f$ ($SiO_2$, EA/n-heptane 2:1)=0.10 MS (DCI): 537 (M+H)

The following Examples 9–14 can be prepared in analogy to the process indicated in Examples 1 and 2 using N-(bromomethyl)phthalimide, N-(3-bromopropyl)phthalimide and N-(4-bromobutyl)phthalimide in place of N-(2-bromoethyl)phthalimide in Example 1a):

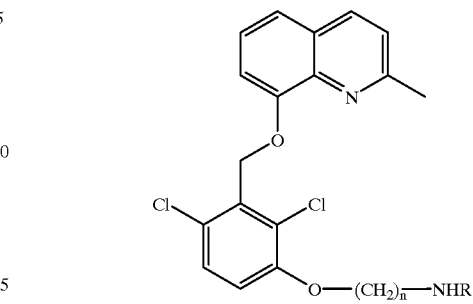

| Example | n | R | MS (DCI) |
|---|---|---|---|
| 9 | 1 | —H | 363 (M + H) |
| 10 | 1 | 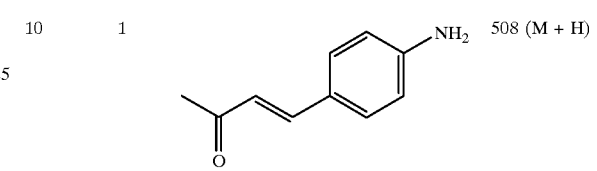 | 508 (M + H) |
| 11 | 3 | —H | 391 (M + H) |
| 12 | 3 | 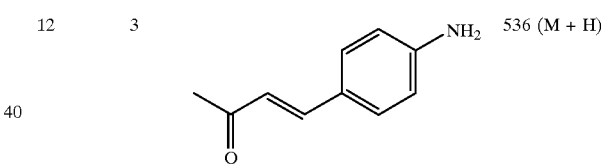 | 536 (M + H) |
| 13 | 4 | —H | 405 (M + H) |
| 14 | 4 | 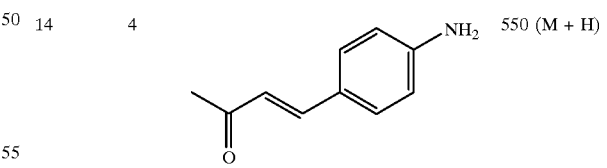 | 550 (M + H) |

Examples 15–20 can be prepared in analogy to the processes indicated in Examples 1 and 2 using 2,5-dimethyl-8-hydroxyquinoline, 2,7-dimethyl-8-hydroxyquinoline and 2,5,7-trimethyl-8-hydroxyquinoline—synthesized as disclosed by H. Fiedler, J. Prakt. Chemie, Vol. 13, 1961, 86 et seq.—in place of 8-hydroxy-2-methylquinoline in Example 1c):

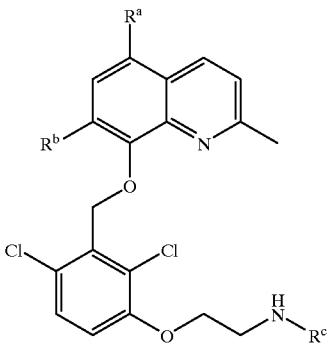

| Example | $R^a$ | $R^b$ | $R^c$ | MS (DCI) |
|---|---|---|---|---|
| 15 | —$CH_3$ | —H | —H | 391 (M + H) |
| 16 | —$CH_3$ | —H | ![structure with NH2] | 536 (M + H) |
| 17 | —H | —$CH_3$ | —H | 391 (M + H) |
| 18 | —H | —$CH_3$ | ![structure with NH2] | 536 (M + H) |
| 19 | —$CH_3$ | —$CH_3$ | —H | 405 (M + H) |
| 20 | —$CH_3$ | —$CH_3$ | ![structure with NH2] | 550 (M + H) |

What is claimed is:

1. A compound of the formula (I),

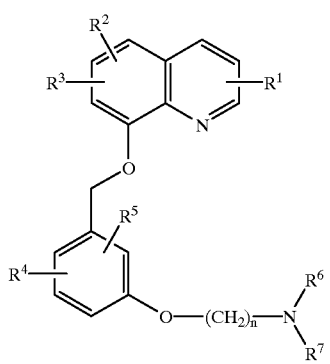

(I)

wherein:

$R^1, R^2, R^3$ identical or different, are
(1) $(C_1-C_5)$-alkyl,
(2) $(C_6-C_{10})$-aryl,
(3) $(C_1-C_3)$-alkyl-$(C_6-C_{10})$-aryl,
(4) halogen,
(5) hydrogen,
(6) $(C_3-C_8)$-cycloalkyl,
(7) CHO,
(8) CO—O—$(C_1-C_3)$alkyl, or
(9) COOH;

$R^4, R^5$ identical or different, are
(1) hydrogen,
(2) halogen,
(3) $(C_1-C_3)$-alkoxy,
(4) nitro,
(5) cyano, or
(6) S—$(C_1-C_3)$-alkyl;

n is a number from 1 to 8;

$R^6$ is
(1) hydrogen,
(2) $(C_1-C_3)$-alkyl,
(3) $(C_3-C_5)$-alkylalkenyl, or
(4) $(C_1-C_3)$-alkyl-$(C_6-C_{10})$-aryl;

17

$R^7$ is hydrogen or the following substituted or unsubstituted acyl radicals:

($C_1$–$C_6$)-alkanoyl, ($C_1$–$C_3$)-alkoxy-($C_2$–$C_6$)-alkanoyl, ($C_1$–$C_6$)-alkylcarbamoyl-($C_2$–$C_6$)alkanoyl, ($C_6$–$C_{12}$)-aryl-($C_2$–$C_6$)-alkanoyl, ($C_3$–$C_7$)-alkenoyl, ($C_3$–$C_8$)-cycloalkylcarbonyl, ($C_5$–$C_7$)-cycloalkenylcarbonyl, ($C_1$–$C_3$)-alkoxycarbonyl, ($C_6$–$C_{12}$)-aryloxycarbonyl, ($C_6$–$C_{12}$)-aroyl, ($C_1$–$C_3$)-alkoxy-($C_6$–$C_{12}$)-aroyl, halogen-($C_6$–$C_{12}$)-aroyl, ($C_6$–$C_{12}$)-aryl-($C_3$–$C_6$)-alkenoyl, ($C_1$–$C_3$)-alkoxy-($C_6$–$C_{12}$)-aryl-($C_3$–$C_6$)-alkenoyl, ($C_1$–$C_3$)-alkylenedioxy-($C_6$–$C_{12}$)-aryl-($C_3$–$C_6$)-alkenoyl, nitro-($C_6$–$C_{12}$)-aryl-($C_3$–$C_6$)-alkenoyl, cyano-($C_6$–$C_{12}$)-aryl-($C_3$–$C_6$)-alkenoyl, halo-($C_6$–$C_{12}$)-aryl-($C_3$–$C_6$)-alkenoyl, halo-($C_1$–$C_3$)-alkyl-($C_6$–$C_{12}$)-aryl-($C_3$–$C_6$)-alkenoyl, hetero-($C_3$–$C_8$)-cycloalkyl-($C_6$–$C_{12}$)-aryl-($C_3$–$C_6$)-alkenoyl, amino-($C_6$–$C_{12}$)-aryl-($C_3$–$C_6$)-alkenoyl, ($C_1$–$C_4$)-alkylamino-($C_6$–$C_{12}$)-aryl-($C_3$–$C_6$)-alkenoyl, ($C_2$–$C_5$)-acylamino-($C_6$–$C_{12}$)-arylcinnamoyl, ($C_1$–$C_3$)-alkoxycarbonylamino-($C_6$–$C_{12}$)-arylcinnamoyl, ($C_1$–$C_4$)-alkylaminocarbonylaminocinnamoyl, hetero-($C_6$–$C_{12}$)-aryl-($C_2$–$C_6$)-alkanoylamino-($C_6$–$C_{12}$)-aryl-($C_3$–$C_6$)-alkenoyl, ($C_6$–$C_{12}$)-aroylamino-($C_6$–$C_{12}$)-aryl-($C_3$–$C_6$)-alkenoyl, hetero-($C_6$–$C_{12}$)-arylcarbonylamino-($C_6$–$C_{12}$)-aryl-($C_3$–$C_6$)-alkenoyl, ($C_1$–$C_5$)alkylsulfonylamino-($C_6$–$C_{12}$)-aryl-($C_3$–$C_6$)-alkenoyl, ($C_1$–$C_5$)-alkylureido-($C_6$–$C_{12}$)-aryl-($C_3$–$C_6$)-alkenoyl, ($C_2$–$C_6$)-alkanoyl-($C_6$–$C_{12}$)-aryl-($C_3$–$C_6$)-alkenoyl, ($C_1$–$C_5$)-alkoxycarbonyl-($C_6$–$C_{12}$)-aryl-($C_3$–$C_6$)-alkenoyl, ($C_1$–$C_5$)-alkylcarbamoyl-($C_6$–$C_{12}$)-aryl-($C_3$–$C_6$)-alkenoyl, ($C_6$–$C_{12}$)-arylcarbamoyl-($C_6$–$C_{12}$)-aryl-($C_3$–$C_6$)-alkenoxyl, ($C_6$–$C_{12}$)-aryl-($C_1$–$C_5$)-alkoxycarbonyl, ($C_1$–$C_5$)-alkylcarbamoyl, ($C_6$–$C_{12}$)-arylcarbamoyl, ($C_6$–$C_{12}$)-aroylcarbamoyl, ($C_1$–$C_6$)-alkylsulfonyl, ($C_6$–$C_{12}$)-arylsulfonyl, ($C_6$–$C_{12}$)-aryl-($C_1$–$C_6$)-alkylsulfonyl, or $R^6$ and $R^7$ together represent a phthaloyl group which forms a ring with the nitrogen atom; or a physiologically toleratedsalt thereof.

2. A compound of the formula (I) as claimed in claim 1, wherein:

$R^1$, $R^2$, $R_3$ identical or dfferent are
(1) hydrogen, or
(2) ($C_1$–$C_3$)-alkyl;
$R^4$, $R^5$ are halogen; and
$R^6$ is
(1) hydrogen,
(2) methyl,
(3) ethyl; or
(4) benzyl;
$R^7$ is same as defined in claim 1,
or a physiologically tolerated salt thereof.

3. A compound of the formula (I) as claimed in claim 1, in which $R^7$ is hydrogen or a physiologically tolerated salt thereof.

4. A compound of the formula (I) as claimed in claim 1, in which $R^7$ is an acyl radical or a physiologically tolerated salt thereof.

5. A compound of the formula (I) as claimed in claim 2, in which $R^7$ is hydrogen or a physiologically tolerated salt thereof.

6. A compound of the formula (I) as claimed in claim 2, in which $R^7$ is an acyl radical or a physiologically tolerated salt thereof.

18

7. A compound of the formula (I) as claimed in claim 1, wherein;

$R^1$, $R^2$, $R^3$ identical or different are
(1) hydrogen,
(2) methyl, or
(3) ethyl;
$R^4$, $R^5$ are chlorine;
n is 1to 4;
$R^6$ is hydrogen; and
$R^7$ is
(1) hydrogen,
(2) ($C_2$–$C_5$)-alkanoyl,
(3) ($C_3$–$C_5$)-alkenoyl,
(4) ($C_1$–$C_5$)-alkylaminocarbonyl,
(5) ($C_6$–$C_{10}$)-aryl-($C_1$–$C_3$)-alkylaminocarbonyl,
(6) ($C_1$–$C_5$)-alkyloxycarbonyl,
(7) ($C_6$–$C_{10}$)-aryl-($C_1$–$C_3$)-alkyloxycarbonyl,
(8) ($C_6$–$C_{10}$)-aryl-($C_3$–$C_7$)-cycloalkylcarbonyl, or
(9) a trans-cinnamic acid residue whose phenyl ring is substituted by up to 2 identical or different radicals selected from
a) hydrogen,
b) ($C_1$–$C_3$)-alkyl,
c) amino,
d) ($C_1$–$C_3$)-mono- and -dialkylamino,
e) halogen,
f) ($C_1$–$C_3$)-haloalkyl,
g) ($C_2$–$C_5$)-acylamino and
h) ($C_1$–$C_3$)-alkoxy; or a physiologically tolerated salt thereof.

8. A compound as claimed in claim 7, or a physiologically tolerated salt thereof, in which n is 2.

9. A compound as claimed in claim 7, or a physiologically tolerated salt thereof, in which $R^7$ is hydrogen.

10. A compound as claimed in claim 7, or a physiologically tolerated salt thereof, in which $R^7$ is ($C_2$–$C_5$)-alkanoyl.

11. A compound as claimed in claim 7, or a physiologically tolerated salt thereof, in which $R^7$ is ($C_1$–$C_5$)-alkylaminocarbonyl.

12. A compound as claimed in claim 7, or a physiologically tolerated salt thereof, in which $R^7$ is ($C_6$–$C_{10}$)-aryl-($C_1$–$C_3$)-alkyloxyarbonyl.

13. A compound as claimed in claim 7, or a physiologically tolerated salt thereof, in which $R^7$ is ($C_6$–$C_{10}$)-aryl-($C_3$–$C_7$)-cycloalkylcarbonyl.

14. A compound as claimed in claim 7, or a physiologically tolerated salt thereof, in which $R^7$ is a trans-cinnamic acid residue whose phenyl ring is substituted by up to 2 identical or different radicals selected from
a) hydrogen,
b) ($C_1$–$C_3$)alkyl,
c) amino,
d) ($C_1$–$C_3$)-mono- and -dialkylamino,
e) halogen,
f) ($C_1$–$C_3$)-haloalkyl,
g) ($C_2$–$C_6$)-acylamino or
h) ($C_1$–$C_3$)-alkoxy.

15. A compound as claimed in claim 14, or a physiologically tolerated salt thereof, in which $R^7$ is a trans-cinnamoyl whose phenyl ring is substituted by up to 2 amino radicals.

16. A compound as claimed in claim 15, or a physiologically tolerated salt thereof, in which $R^7$ is a trans-4-aminocinnamoyl.

17. A pharmaceutical composition comprising a compound as claimed in claim 1, or a physiologically tolerated salt thereof.

18. A method of treating pain comprising administering an effective amount of a compound as claimed in claim 1, or a physiologically tolerated salt thereof.

19. A compound as claimed in claim 1, in which the compound is 8-(3-(2-aminoethoxy)-2,6-dichlorobenzyloxy)-2-methylquinoline, or a physiologically tolerated salt thereof.

20. A compound as claimed in claim 1, in which the compound is 8-(3-(2-N-(trans-4-aminocinnamoyl)aminoethoxy)-2,6-dichlorobenzyloxy)-2-methylquinoline, or a physiologically tolerated salt thereof.

21. A compound as claimed in claim 1, in which the compound is 8-(2,6-dichloro-3-(2-(N-ethylaminocarbonylamino)ethoxy)benzyloxy)-2-methylquinoline, or a physiologically tolerated salt thereof.

22. A compound as claimed in claim 1, in which the compound is 8-(2,6-dichloro-3-(2-(3-phenylpropionylamino)ethoxy)benzyloxy)-2-methylquinoline, or a physiologically tolerated salt thereof.

23. A compound as claimed in claim 1, in which the compound is 8-(2,6-dichloro-3-(trans-2-N-cinnamoylaminoethoxy)benzyloxy)-2-methylquinoline, or a physiologically tolerated salt thereof.

24. A compound as claimed in claim 1, in which the compound is 8-(2,6-dichloro-3-(2-N-(trans-4-methoxycinnamoyl)aminoethoxy)benzyloxy)-2-methylquinoline, or a physiologically tolerated salt thereof.

25. A compound as claimed in claim 1, in which the compound is 8-(2,6-dichloro-3-(2-(N-(trans-2-phenylcyclopropane-1-carbonylamino)-ethoxy)benzyloxy)-2-methylquinoline, or a physiologically tolerated salt thereof.

26. A compound as claimed in claim 1, in which the compound is 8-(2,6-dichloro-3-(2-N-(trans-3-methoxycinnamoyl)aminoethoxy)-benzyloxy)-2-methyquinoline, or a physiologically tolerated salt thereof.

27. A compound as claimed in claim 1, in which the compound is 8-(3-(2-aminomethoxy)-2,6-dichlorobenzyloxy)-2-methylquinoline, or a physiologically tolerated salt thereof.

28. A compound as claimed in claim 1, in which the compound is 8-(3-(2-N-(trans-4-aminocinnamoyl)aminomethoxy)-2,6-dichlorobenzyloxy)-2-methylquinoline, or a physiologically tolerated salt thereof.

29. A compound as claimed in claim 1, in which the compound is 8-(3-(2-aminopropoxy)-2,6-dichlorobenzyloxy)-2-methylquinoline, or a physiologically tolerated salt thereof.

30. A compound as claimed in claim 1, in which the compound is 8-(3-(2-N-(trans-4-aminocinnamoyl)aminopropoxy)-2,6-dichlorobenzyloxy)-2-methylquinoline, or a physiologically tolerated salt thereof.

31. A compound as claimed in claim 1, in which the compound is 8-(3-(2-aminobutoxy)-2,6-dichlorobenzyloxy)-2-methylquinoline, or a physiologically tolerated salt thereof.

32. A compound as claimed in claim 1, in which the compound is 8-(3-(2-N-(trans-4-aminocinnamoyl)aminobutoxy)-2,6-dichlorobenzyloxy)-2-methylquinoline, or a physiologically tolerated salt thereof.

33. A compound as claimed in claim 1, in which the compound is 8-(3-(2-aminoethoxy)-2,6-dichlorobenzyloxy)-2,5-dimethylquinoline, or a physiologically tolerated salt thereof.

34. A compound as claimed in claim 1, in which the compound is 8-(3-(2-N-(trans-4-aminocinnamoyl)aminoethoxy)-2,6-dichlorobenzyloxy)-2,5-dimethylquinoline, or a physiologically tolerated salt thereof.

35. A compound as claimed in claim 1, in which the compound is 8-(3-(2-aminoethoxy)-2,6-dichlorobenzyloxy)-2,7-dimethylquinoline, or a physiologically tolerated salt thereof.

36. A compound as claimed in claim 1, in which the compound is 8-(3-(2-N-(trans-4-aminocinnamoyl)aminoethoxy)-2,6-dichlorobenzyloxy)-2,7-dimethylquinoline, or a physiologically tolerated salt thereof.

37. A compound as claimed in claim 1, in which the compound is 8-(3-(2-aminoethoxy)-2,6-dichlorobenzyloxy)-2,5,7-trimethylquinoline, or a physiologically tolerated salt thereof.

38. A compound as claimed in claim 1, in which the compound is 8-(3-(2-N-(trans-4-aminocinnamoyl)aminoethoxy)-2,6-dichlorobenzyloxy)-2,5,7-trimethylquinoline, or a physiologically tolerated salt thereof.

* * * * *

UNITED STATES PATENT AND TRADEMARK OFFICE
CERTIFICATE OF CORRECTION

PATENT NO.    : 6,140,341
DATED         : October 31, 2000
INVENTOR(S)   : Holger Heitsch et al.

It is certified that error appears in the above-identified patent and that said Letters Patent is hereby corrected as shown below:

<u>Title page,</u>
Item [75], in the Inventors,
Line 3, "Schölkens" should read -- Schölkens --;
Line 4, "Nölken" should read -- Nölken --.

<u>Column 17, claim 1,</u>
Line 28, "($C_1$-$C_5$)alkylsulfonylamino" should read -- ($C_1$-$C_5$)-alkylsulfonylamino --.
Line 41, "toleratedsalt" should read -- tolerated salt --.

<u>Column 17, claim 2,</u>
Line 45, "$R_3$" should read -- $R^3$ --.

<u>Column 18, claim 7,</u>
Line 2, "wherein;" should read -- wherein: --.

<u>Column 18, claim 12,</u>
Line 42, "alkyloxyarbonyl" should read -- alkyloxycarbonyl --.

<u>Column 18, claim 14,</u>
Line 57, "($C_2$-$C_6$)-acylamino" should read -- ($C_2$-$C_5$)-acylamino --.

<u>Column 19, claim 26,</u>
Line 36, "methyquinoline" should read -- methylquinoline --.

Signed and Sealed this

Twenty-ninth Day of January, 2002

*Attest:*

*Attesting Officer*

JAMES E. ROGAN
*Director of the United States Patent and Trademark Office*